United States Patent
Xie et al.

(10) Patent No.: US 7,232,870 B2
(45) Date of Patent: Jun. 19, 2007

(54) BRIDGED METALLOCENE COMPLEXES, PROCESS FOR PREPARING THE SAME AND USE THEREOF

(75) Inventors: Zuowei Xie, Hong Kong (CN); Yaorong Wang, Suzhou (CN); Yuepeng Cai, Shenzhen (CN)

(73) Assignee: The Chinese University of Hong Kong, Hong Kong (CN)

( * ) Notice: Subject to any disclaimer, the term of this patent is extended or adjusted under 35 U.S.C. 154(b) by 292 days.

(21) Appl. No.: 11/083,498

(22) Filed: Mar. 18, 2005

(65) Prior Publication Data

US 2005/0215739 A1 Sep. 29, 2005

Related U.S. Application Data

(60) Provisional application No. 60/556,417, filed on Mar. 25, 2004.

(51) Int. Cl.
*C08F 4/64* (2006.01)
*C08F 4/6192* (2006.01)
*C07F 17/00* (2006.01)

(52) U.S. Cl. ............. 526/134; 526/170; 556/7; 556/8; 556/53; 568/3; 502/152; 502/158; 502/202

(58) Field of Classification Search .............. 556/7, 556/8, 53; 566/3; 502/152, 158, 202; 526/136, 526/170

See application file for complete search history.

(56) References Cited

U.S. PATENT DOCUMENTS 5,162,466 A 11/1992 Karol et al.
5,214,173 A * 5/1993 Jordan et al. ............... 556/8

OTHER PUBLICATIONS

Hong et al. "A Neutral Group 4, Poly(methyl methacrylate) Catalyst Derived from o-Carborane", Organometallics, vol. 17, Jul. 1998, pp. 2933-2935.*

D.J. Crowther, et al., "Group 4 Metal Dicarbollide Chemistry. Synthesis, Structure, and Reactivity of Electrophilic Alkyl Complexes $(Cp^*)(C_2B_9H_{11})M(R)$ (M=Hf, Zr)," *J. Am. Chem. Soc.* 1991, 113, 1455-1457.

J.A. Gladysz, Guest Editor, Special Issue for "Frontiers in Metal-Catalyzed Polymerization: Designer Metallocenes, Designs on New Monomers, Demystifying MAO, Metathesis Déshabillé," *Chemical Reviews*, vol. 100, No. 4, Apr. 2000, pp. 1167-1168, and pp. 1-3 of Table of Contents.

W. Kaminsky, et al., "Metallocenes for Polymer Catalysis," *Adv. Polym. Sci.*, 1997, 127, 142-187.

* cited by examiner

*Primary Examiner*—Caixia Lu
(74) *Attorney, Agent, or Firm*—Knobbe, Martens, Olson & Bear, LLP (57) ABSTRACT

Provided is a bridged cyclopentadienyl-dicarbollide complex having the formula of $\{L[(Cp)(C_2B_9R^1{}_{10})]\}MR$ in which Cp is an unsubstituted, alkyl-substituted, aryl-substituted or fused ring cyclopentadienyl, $R^1$ is hydrogen, or alkyl, L is a bridging unit that bonds to both Cp ring and cage carbon atoms, R is alkyl, aryl or a derivative thereof and M is Ti, Zr or Hf. A process for preparing the complex disclosed herein is also provided.

24 Claims, 4 Drawing Sheets represents Cp group in formula (I)
M' = alkali metals

FIGURE 1

M = Ti, Zr, Hf;
R = CH$_2$Ph, CH$_2$SiMe$_3$, NHC$_6$H$_3$Me$_2$-2,6;
Y = Li, Na, K.

BRIDGED METALLOCENE COMPLEXES, PROCESS FOR PREPARING THE SAME AND USE THEREOF

CROSS REFERENCE TO RELATED APPLICATIONS

This application claims the benefit of U.S. Provisional Application No. 60/556,417 filed Mar. 25, 2004, which is explicitly incorporated herein by reference in its entirety.

FIELD OF THE INVENTION

The present invention relates to metallocene complexes which are very active for olefin polymerization. Particularly, the invention relates to bridged metallocene complexes used as a single component of Ziegler-Natta catalysts in chemical industry for replacing conventional metallocene/MAO systems without alteration of existing plants.

BACKGROUND OF THE INVENTION

Existing Group IVB metallocene catalysts for olefin polymerization generally consist of two components, precatalysts and cocatalysts. The precatalyst includes a Group IVB metallocene dichloride or a dialkyl complex composed of two aromatic five-membered ring systems that may be tethered by a bridging unit (ansa metallocene complexes). Aromatic ligands to Group IVB metal can be of the same or different type, including but not limited to: cyclopentadienyl, indenyl, fluorenyl, or their derivatives. The cocatalysts includes normally alumoxane (MAO), modified alumoxane (MMAO) or perfluoro (tetraphenyl)borate. The precatalyst does not show any activity toward olefin polymerization. The cocatalyst is essential to activate the precatalyst.

Al(MAO)/M(Group IVB metal) molar ratio of 1,000 in a Group IVB metallocene catalyst is typical but it can reach 20,000 in some cases (Kaminsky, W.; Arndt, M. *Adv. Polym. Sci.* 1997, 127, 144; Gladysz, J. A. Guest Editor, Special Issue for Frontiers in Metal-Catalyzed Polymerization. *Chem. Rev.* 2000, 100 (4)). The disadvantage of the current catalyst system is the incorporation of aluminum or fluorine into the polymer, which can cause serious problems when polyolefins are thermally decomposed.

To overcome these problems, a neutral Group IVB metallocene type of catalysts containing dicarbollide, [($C_5Me_5$)($C_2B_9H_{11}$)]MMe (M=Ti, Zr, Hf), was developed. Fourteen electron, $d^0$ bent-metallocene alkyl complexes of general type $(C_5R_5)_2M(R')^+$ exhibit a rich insertion, olefin polymerization, and C—H activation chemistry which is highly sensitive to the structural and electronic properties of the $(C_5R_5)_2M$ fragment, the presence or absence of Lewis base, and counterion/cocatalyst properties. Replacement of a uninegative $C_5R_5^-$ ligand of $(C_5R_5)_2M(R')^+$ by the isolobal, di-negative dicarbollide ligand $(C_2B_9H_{11}^{2-})$ reduces the overall charge by one unit but leaves the gross structural and metal frontier orbital properties unchanged.

The resulting neutral mixed sandwich complexes [($C_5Me_5$)($C_2B_9H_{11}$)]M(R) show a variety of ligand exchange, insertion (alkenes, alkynes etc) and ligand C—H activation reactions characteristics of electrophilic metal alkyls (Crowther, D. J.; Baenziger, N. C.; Jordan. R. F. *J. Am. Chem. Soc.* 1991, 113, 1455). It is noteworthy that this type of complexes can catalyze the polymerization of ethylene with a moderate activity in the absence of any cocatalysts. The activity was $7.2 \times 10^4$ g of PE/(mol of Zr atom h)(Crowther, D. J.; Baenziger, N. C.; Jordan. R. F. *J. Am. Chem. Soc.* 1991, 113, 1455). The activity would be increased in the presence of $R_3Al$ (R=alykl).

[($C_5Me_5$)($C_2B_9H_{11}$)]MMe are not thermally stable and can be converted into $\{[(C_5Me_5)(C_2B_9H_{11})]M\}_2CH_2$ upon heating. The latter is also an active catalyst for ethylene polymerization with a similar activity to its parent complex (Crowther, D. J.; Baenziger, N. C.; Jordan. R. F. *J. Am. Chem. Soc.* 1991, 113, 1455; Karol, F. J.; Kao, S.-C.; Brady III, R. C. U.S. Pat. No. 5,162,466), which is a significant progress in the field of Ziegler-Natta catalysis (Kaminsky, W.; Arndt, M. *Adv. Polym. Sci* 1997, 127, 144). This process is of great scientific and technological interests since it can avoid using expense MAO, thus eliminating possible contaminate of alumina in the polymeric materials. However, these catalysts cannot be used in industries due to low activities.

SUMMARY OF THE INVENTION

We have recently developed a linked cyclopentadienyl-dicarbollide ligand system in which the ansa-ligand renders a Group IVB metal complex in a more open coordination sphere, which in turn not only increases significantly catalytic activities in olefin polymerization in comparison with non-bridged systems, but also improves greatly thermal stability of the catalyst itself.

One aspect of the present invention is to provide a novel Group IVB bridged metallocene complex having the formula (I):

$$\{L[(Cp)(C_2B_9R^1{}_{10})]\}MR \qquad (I)$$

wherein

Cp is selected from the group consisting of cyclopentadienyl, indenyl, tetrahydroindenyl, and fluorenyl, unsubstituted or substituted by one or more radicals selected from the group consisting of $C_1$–$C_{10}$ alkyl, $C_2$–$C_{10}$ alkenyl, $C_3$–$C_{10}$ cycloalkyl, $C_1$–$C_{10}$ alkoxy, and $C_6$–$C_{15}$ aryl, where each pair of adjacent radicals on the ring together may form a cyclic group;

each $R^1$ is independently hydrogen, halogen, $C_1$–$C_{10}$ alkyl or $C_2$–$C_{10}$ alkenyl;

L is $C_1$–$C_4$ alkylene unsubstituted or substituted by one or more radicals selected form the group consisting of $C_1$–$C_{10}$ alkyl, $C_2$–$C_{10}$ alkenyl, $C_3$–$C_{10}$ cycloalkyl, $C_1$–$C_{10}$ alkoxy and $C_6$–$C_{15}$ aryl, or $Si(R^2)_2$ where each $R^2$ is independently selected from the group consisting of hydrogen, $C_1$–$C_{10}$ alkyl, $C_2$–$C_{10}$ alkenyl, $C_1$–$C_{10}$ alkoxy, $C_3$–$C_{10}$ cycloalkyl, and $C_6$–$C_{15}$ aryl, that bonds to both the Cp ring and the cage of $C_2B_9R^1{}_{10}$;

R is selected from the group consisting of hydrogen, halogen, $R^3$, $OR^3$, $SR^3$, $NR^3R^4$, $PR^3R^4$, and $ZSiR_3(R^4)_2$ where each $R^3$ is independently selected from the group consisting of $C_1$–$C_{10}$ alkyl, $C_2$–$C_{10}$ alkenyl, $C_3$–$C_{10}$ cycloalkyl and $C_6$–$C_{15}$ aryl, and each $R^4$ is independently selected from the group consisting of hydrogen, $C_1$–$C_{10}$ alkyl, $C_2$–$C_{10}$ alkenyl, $C_3$–$C_{10}$ cycloalkyl and $C_6$–$C_{15}$ aryl, and Z is $C_1$–$C_{10}$ alkylene; and M is Ti, Zr or Hf.

According to another aspect of the present invention, there is provided a method for the preparation of a bridged metallocene complex of the formula (I), which comprises:

reacting a protonated form of $\{L[(Cp)(C_2B_9R^1{}_{10})]\}^{3-}$ with $MR_4$ where R is defined above but not halogen, alternatively reacting {L[(Cp)(C$_2$B$_9$R$^1$$_{10}$)]}$^{3-}$ with MX$_4$ and, if desired, followed by the substitution of X with R where R is defined above but not halogen, wherein X is halogen, and Cp, L, R$^1$ and M are as defined above.

A further aspect of the present invention relates to a process for olefin polymerization comprising contacting one or more olefin monomers with a complex of formula (I).

In some preferred embodiments of the invention, the substituents on the Cp are selected from the group consisting of C$_1$–C$_4$ alkyl, C$_2$–C$_4$ alkenyl, C$_3$–C$_6$ cycloalkyl, C$_1$–C$_4$ alkoxy, C$_6$–C$_{10}$ aryl. Moreover, each pair of adjacent radicals on the ring together may also form a cyclic group.

In more preferred embodiments, Cp is unsubstituted cyclopentadienyl or indenyl or substitiuted by from one to four substitutes selected from the group consisting of C$_1$ to C$_4$ alkyl, C$_2$ to C$_4$ alkenyl, C$_3$ to C$_6$ cycloalkyl, C$_1$ to C$_4$ alkoxy and C$_6$–C$_{10}$ aryl. Particular substituents on the Cp are selected from the group consisting of methyl, isopropyl and tert-butyl.

In the invention, R$^1$ is preferably hydrogen.

In preferred embodiments of the invention, L is C$_1$–C$_4$ alkylene unsubstituted or substituted by one or more radicals selected from the group consisting of C$_1$–C$_4$ alkyl, C$_2$–C$_4$ alkenyl, C$_3$–C$_6$ cycloalkyl, C$_1$–C$_4$ alkoxy, and C$_6$–C$_{10}$ aryl, or Si(R$^2$)$_2$ where each R$^2$ is independently selected from the group consisting of hydrogen, C$_1$–C$_4$ alkyl, C$_2$–C$_4$ alkenyl, C$_3$–C$_6$ cycloalkyl, C$_1$–C$_4$ alkoxy, and C$_6$–C$_{10}$ aryl. More preferably, L is unsubstituted C$_1$–C$_2$ alkylene or substituted by two substitutes selected from C$_1$–C$_4$ alkyl. In a specifically preferred embodiment, L is C(CH$_3$)$_2$.

R is preferably selected from the group consisting of R$^3$, OR$^3$, SR$^3$, NR$^3$R$^4$, PR$^3$R$^4$ and ZSiR$^3$(R$^4$)$_2$ where each R$^3$ is independently selected from the group consisting of C$_1$–C$_4$ alkyl, C$_2$–C$_4$ alkenyl, C$_3$–C$_6$ cycloalkyl, and C$_6$–C$_8$ aryl, and each R$^4$ is independently selected from the group consisting of hydrogen, C$_1$–C$_4$ alkyl, C$_2$–C$_4$ alkenyl, C$_3$–C$_6$ cycloalkyl, and C$_6$–C$_8$ aryl, and Z is C$_1$–C$_4$ alkylene. More preferably, R is selected from the group consisting of R$^3$, OR$^3$, NR$^3$R$^4$ and ZSiR$^3$(R$^4$)$_2$ where each R$^3$ is independently selected from the group consisting of C$_1$–C$_4$ alkyl and C$_6$–C$_8$ aryl, and each R$^4$ is independently selected from the group consisting of hydrogen, C$_1$–C$_4$ alkyl and C$_6$–C$_8$ aryl, and Z is C$_1$–C$_4$ alkylene.

In the invention, M is preferably Zr or Hf.

In further some specific embodiments, M is Zr or Hf, Cp is C$_5$H$_4$, C$_5$Me$_4$, C$_5$H$_2$(Pr$^i$)$_2$, C$_5$H$_2$(Bu$^t$)$_2$ or C$_9$H$_6$, L is CMe$_2$, R$^1$ is hydrogen and R is CH$_2$Ph, CH$_2$TMS or NHC$_6$H$_3$Me$_2$-2,6.

In the process of the invention, the olefin monomer is preferably an alpha-olefin.

Complexes of formula (I) according to the invention can be used as a sole active component of a catalyst for olefin polymerization with high activity. In a specific embodiment of the invention, the activity of a complex of formula (I) is 4.64×10$^6$ g of PE/(mol of Zr atom-h) in the absence of any cocatalysts. The complexs of the invention as catalysts for olefin polymerization are of good thermal stability, and can be employed in chemical industry without alteration of existing plants.

BRIEF DESCRIPTION OF THE DRAWINGS

For the purpose of illustration, there are depicted in the drawings certain preferred embodiments of the invention. However, the invention is not limited to precise methods and complexes of the embodiments depicted in the drawings. In the drawings.

DETAILED DESCRIPTION OF THE INVENTION

According to an aspect of the present invention, there are provided bridged cyclopentadienyl-dicarbollide metallocene complexs of formula (I):

{L[(Cp)(C$_2$B$_9$R$^1$$_{10}$)]}MR    (I)

wherein:

Cp is selected from the group consisting of cyclopentadienyl, indenyl, tetrahydroindenyl, and fluorenyl, unsubstituted or substituted by one or more radicals selected from the group consisting of C$_1$–C$_{10}$ alkyl, C$_2$–C$_{10}$ alkenyl, C$_3$–C$_{10}$ cycloalkyl, C$_1$–C$_{10}$ alkoxy, and C$_6$–C$_{15}$ aryl, where each pair of adjacent radicals on the ring together may form a cyclic group;

each R$^1$ is independently hydrogen, halogen, C$_1$–C$_{10}$ alkyl or C$_2$–C$_{10}$ alkenyl;

L is C$_1$–C$_4$ alkylene unsubstituted or substituted by one or more radicals selected form the group consisting of C$_1$–C$_{10}$ alkyl, C$_2$–C$_{10}$ alkenyl, C$_3$–C$_{10}$ cycloalkyl, C$_1$–C$_{10}$ alkoxy and C$_6$–C$_{15}$ aryl, or Si(R$^2$)$_2$ where each R$^2$ is independently selected from the group consisting of hydrogen, C$_1$–C$_{10}$ alkyl, C$_2$–C$_{10}$ alkenyl, C$_1$–C$_{10}$ alkoxy, C$_3$–C$_{10}$ cycloalkyl, and C$_6$–C$_{15}$ aryl, that bonds to both Cp ring and the cage of C$_2$B$_9$R$^1$$_{10}$;

R is selected from the group consisting of hydrogen, halogen, R$^3$, OR$^3$, SR$^3$, NR$^3$R$^4$, PR$^3$R$^4$, and ZSiR$_3$(R$^4$)$_2$ where each R$^3$ is independently selected from the group consisting of C$_1$–C$_{10}$ alkyl, C$_2$–C$_{10}$ alkenyl, C$_3$–C$_{10}$ cycloalkyl and C$_6$–C$_{15}$ aryl, and each R$^4$ is independently selected from the group consisting of hydrogen, C$_1$–C$_{10}$ alkyl, C$_2$–C$_{10}$ alkenyl, C$_3$–C$_{10}$ cycloalkyl and C$_6$–C$_{15}$ aryl, and Z is C$_1$–C$_{10}$ alkylene; and M is Ti, Zr or Hf.

In the invention, the term "alkyl" means straight or branched saturated acyclic radical.

The term "alkenyl" means straight or branched unsaturated acyclic radical with one or more double-bonds.

The term "cycloalkyl" refers to saturated cyclic alkyl.

The term "aryl" means unsaturated radical containing at least three double-bonds and constituting a conjugated system.

"C$_2$B$_m$R$^1$$_n$" referred to herein means a dicarbollide or a radical or a negative ion thereof (m=9 or 10, n=10, 11, 12, 13).

Other technical terms or phrases used herein, unless otherwise specified, should be deemed to have the same meaning as those in the art.

As used herein, the following abbreviations have the following meanings. Any abbreviations not defined have their generally accepted meaning.

Me means methyl; $Pr^i$ means isopropyl; $Bu^t$ means tert-butyl; Ph means phenyl; and TMS means $SiMe_3$.

A particularly interesting class of metallocenes according to the invention is that of the complexes of formula (I) in which the Cp is $C_5H_4$, $C_5Me_4$, $C_5H_2(Bu^t)_2$, indenyl or fluorenyl, L is $CMe_2$, $CH_2$ or $Si(CH_3)_2$, and M is Zr or Hf.

Referring to FIGS. 1–4, the present invention is to provide a method for the preparation of bridged metallocene complexes of the formula (I), which comprises:

reacting a protonated form of $\{L[(Cp)(C_2B_9R^1{}_{10})]\}^{3-}$ with $MR_4$ wherein Cp, L, $R^1$ and M are as above defined, and R is the same as defined above, but not halogen, alternatively reacting $\{L[(Cp)(C_2B_9R^1{}_{10})]\}^{3-}$ with $MX_4$ and, if desired, followed by the substitution of X with R wherein X is halogen and R is the same as defined above but not halogen, and Cp, L, $R^1$ and M are as above defined.

The reaction of substitution of substituents X with substituents R that are defined above but not halogen can be carried out by methods well-known to those skilled in the art. For example, when the desired R substituents are alkyl groups, the metallocenes can be made to react with alkyl-magnesium halides (Grignard reagents) or with alkali metal alkyl compounds.

Suitable solvent for the method of the invention is a hydrocarbon solvent such as, for example hexane, cyclohexane, heptane, pentane, toluene or a cyclic or acyclic ether such as diethyl ether, tetrahydrofuran, glymes (e.g. dimethoxyethane), di-n-butyl ether, dioxane, di-isopropyl ether and the like, or a mixture thereof. Preferably, toluene, pentane, tetrahydrofuran or a mixture thereof is used.

In general, an amount of the solvent used ranging from 1 to about 20 times, preferably from 10 to 15 times, the weight of reactants can be effectively employed. However, those skilled in the art will know well that a greater amount of the solvent can also be employed.

The method for preparing a complex of the formula (I) is readily performed at a temperature ranging from as low as about –100° C. to as high as about room temperature. It is preferred to take the reaction at a temperature below room temperature. The reactants are mixed more preferably below –50° C., most preferably below –78° C., and then warmed to room temperature.

Figure 1:
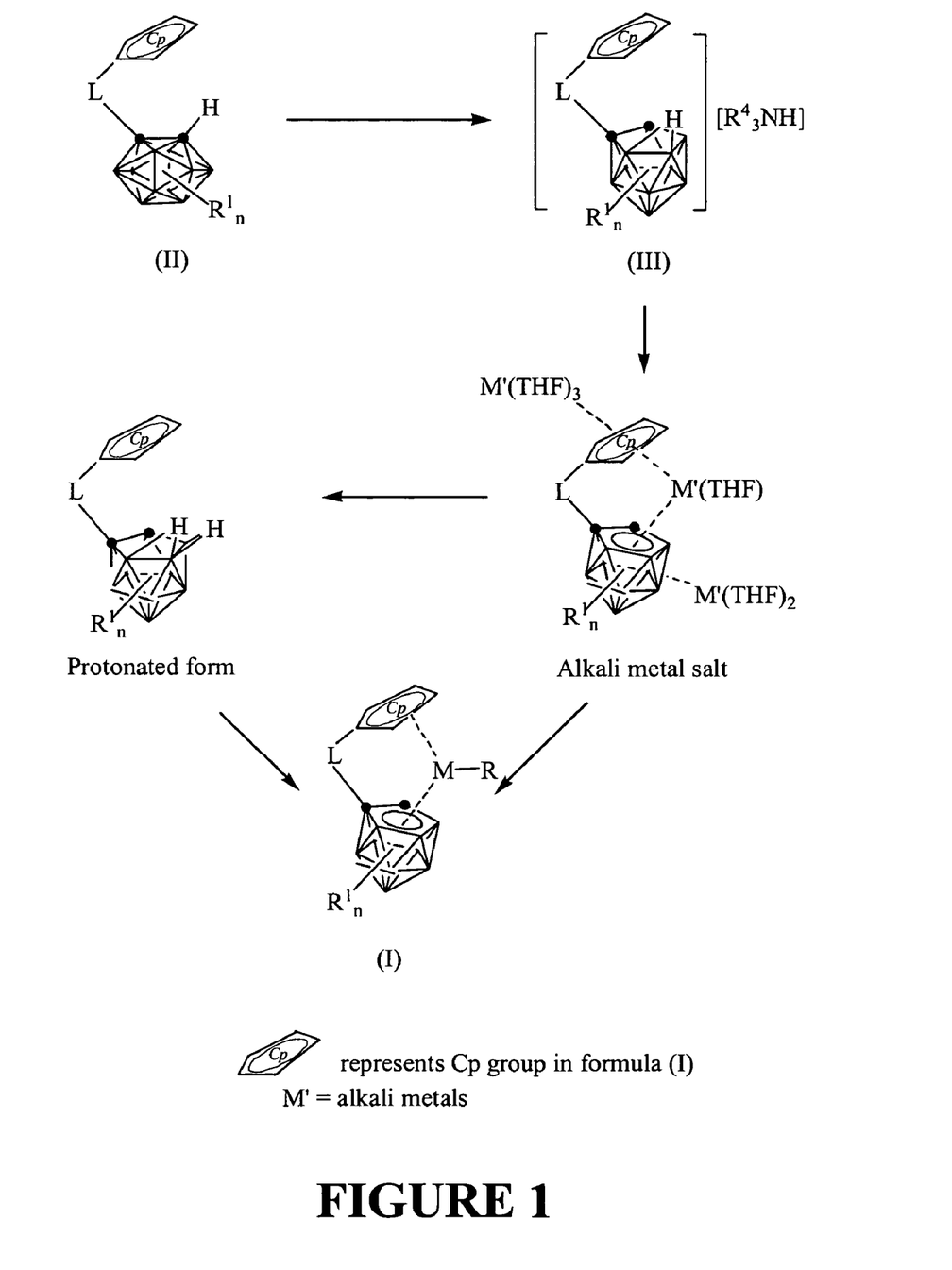
FIG. 1 illustrates a preferred reaction scheme for producing a bridged cyclopentadienyl dicarbollide metallocene complex of formula (I) using a bridged cyclopentadienyl dicarbollide complex as a starting material.

As shown in FIG. 1, in a preferred embodiment, said $\{L[(Cp)(C_2B_9R^1{}_{10})]\}^{3-}$ is an alkali metal salt of a bridged cyclopentadienyl-dicarbollide ligand of formula (II):

(II)

wherein L, Cp and $R^1$ are as defined above.

The ligand of the formula (II) can be prepared following the methods in Xie, Z. Acc. Chem. Res. 2003, 36, 1, which is incorporated herein by reference, for example by reacting an unsubstituted or substituted fulvene with a lithium dicarbollide at the presence of an acid.

The alkali metal salt of a ligand of the formula (II) can be prepared by reacting alkali metal alkyls or alkali metal hydrides with a complex of formula (III):

(III)

wherein $R^5$ is alkyl, preferably $C_1$–$C_6$ alkyl, and Cp, L and $R^1$ are as above defined.

The complex of the formula (III) can be prepared by reacting a ligand of formula (II) with $R_3{}^5NHX$, wherein X is halogen, and $R^5$ is as above defined.

In a further preferred embodiment, the alkali metal salt is a sodium salt and the process for preparing a bridged metallocene complex is performed with $MCl_4$ and RY in the solution of THF, wherein M is Ti, Zr or Hf, Y is an alkali metal and the group R is $CH_2Ph$, $CH_2SiMe_3$ ($CH_2TMS$) or $NHC_6H_3Me_2$-2,6.

In another preferred embodiment, the protonated form of $\{L[(Cp)(C_2B_9R^1{}_{10})]\}^{3-}$ (as shown in FIG. 1) can be obtained by treating the alkali metal salt of a ligand of the formula (II) with an acid such as $H_3PO_4$.

The present invention also relates to a process for olefin polymerization comprising contacting one or more olefin monomers with a complex of the formula (I). In the process for the polymerization of olefins according to the invention, the olefin monomer may the same or different. Preferred olefinic monomers are ethylene, alpha olefins such as propylene and 1-butene, cycloolefins and conjugated diolefins, having two to eight carbon atoms. More preferably, the olefin used is ethylene and an alpha olefin including propylene, butane-1, petene-1, and hexene-1.

The complex of the formula (I) can be used in the polymerization directly or by depositing the complex of the formula (I) on inert supports, such as silica, alumina, styrene-divinylvenzene copolymers or polyehtylene.

The amount of the complex of the formula (I) used in the polymerization is well known for those skilled in the art. Generally, a catalytic amount of a complex of the formula (I) will be enough for the polymerization.

Polyethylene has been used in food packaging, coatings, countless molded toys, and other household items, and it is finding its way into the market to replace common materials such as glass, metal, paper, and concrete. The demand for polyethylene has reached 50 million metric tons annually. This invention relates to novel Group IVB metallocene catalysts showing a very high activity in ethylene polymerization under standard testing conditions in the absence of a cocatalyst and there is a possibility for these catalysts to be used in chemical industry without alteration of existing plant. Therefore, this invention will certainly interest polyethylene producers and catalysts makers.

The following examples are designed to illustrate the present invention and are not intended as a limitation upon the scope thereof.

EXAMPLE 1

Preparation of $[Me_2C(C_5H_5)(C_2B_9H_{11})][Me_3NH]$

Figure 2:
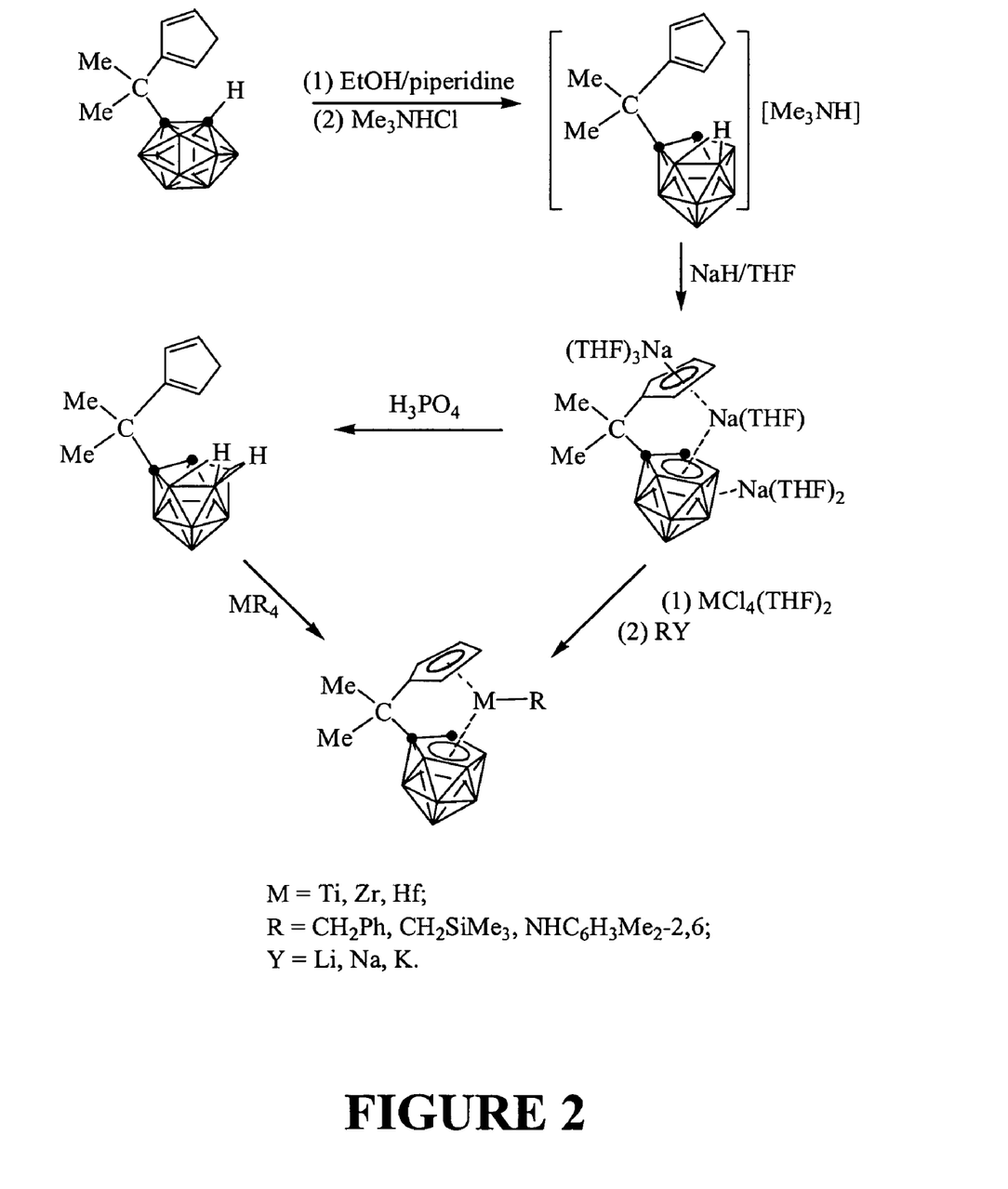
FIG. 2 illustrates a preferred reaction scheme for producing complexes of formula (I) using a bridged cyclopentadienyl dicarbollide complex as a starting material.

As shown in FIG. 2, to an ethanol (40 mL) solution of $Me_2C(C_5H_5)(C_2B_{10}H_{11})$ (0.75 g, 3.0 mmol) was added piperidine (7.5 mL, 75.0 mmol). The mixture was refluxed for 2 days. After removal of ethanol and excess piperidine under vacuum, the residue was dissolved in ethanol (5 mL). A saturated trimethylammonium hydride chloride solution was added to give a sticky solid. Recrystallization from acetone/ether afforded colorless crystals (0.72 g, 80%).

$^1$H NMR (acetone-$d_5$): δ 6.72 (m), 6.31 (m), 6.24 (m), 6.18 (m), 6.06 (m), 5.88 (m)(3H, $C_5H_5$, indicating a mixture of allylic and vinylic isomers), 2.99 (s, 9H)(($CH_3$)$_3$NH), 2.82 (m, 2H)($C_5H_5$), 1.68 (s, 1H)(CH of $C_2B_9H_{11}$), 1.24 (s, 3H), 1.08 (br s, 1H)(B—H—B).

$^{13}$C NMR (acetone-d$_6$): δ 161.3, 158.1, 136.0, 132.5, 132.0, 131.0, 124.7, 124.0 (C$_5$H$_5$), 45.4 ((CH$_3$)$_3$NH), 42.9 (C$_5$H$_5$), 41.0, 31.3 ((CH$_3$)$_2$C).

$^{11}$B NMR (acetone-d$_6$): δ −11.1 (2), −16.1 (2), −18.1 (1), −19.4 (1), −22.8 (1), −33.4 (1), −36.8 (1).

IR (KBr, cm$^{-1}$): ν 3128 (m), 2965 (m), 2514 (vs), 2313 (w), 1615 (m), 1465 (s), 1377 (m), 1262 (w), 1180 (w), 1027 (m), 982 (m), 797 (m).

Calculated for C$_{13}$H$_{32}$B$_9$N: C, 52.10; H, 10.76; N, 4.67; and found: C, 51.78; H, 10.69; N, 4.88.

EXAMPLE 2

Preparation of [{[(μ-η$^5$): η$^5$-Me$_2$C(C$_5$H$_4$)(C$_2$B$_9$H$_{10}$)]Na(THF)}{Na(THF)$_3$}{Na(THF)$_2$}]$_2$ To a THF (30 mL) solution of [Me$_2$C(C$_5$H$_5$)(C$_2$B$_9$H$_{11}$)][Me$_3$NH] (0.47 g, 1.58 mmol) was added NaH (0.32 g, 13.3 mmol) and the reaction mixture was refluxed for 2 days. The excess of NaH was filtered off. The resulting clear brown solution was concentrated to about 10 mL. The title complex was isolated as colorless crystals after this solution stood at room temperature for several days (0.62 g, 51%).

$^1$H NMR (pyridine-d$_5$): δ 6.58 (m, 2H), 6.37 (m, 2H) (C$_5$H$_4$), 3.66 (m, 28H) (THF), 2.10 (s, 1H)(CH of C$_2$B$_9$H$_{10}$), 1.90 (s, 3H)((CH$_3$)$_2$C), 1.63 (m, 31H) (THF+(CH$_3$)$_2$C).

$^{13}$C NMR (pyridine-d$_5$): δ 101.2, 100.9, 100.8 (C$_5$H$_4$), 67.2, 25.2 (THF), 61.4 (C$_2$B$_9$H$_{10}$), 31.1, 30.2, 29.9 ((CH$_3$)$_2$C).

$^{11}$B NMR (pyridine-d$_5$): δ −21.0 (6), −24.6 (2), −44.9 (1).

IR (KBr, cm$^{-1}$): ν 2962 (s), 2914 (m), 2879 (m), 2503 (vs), 2350 (w), 1637 (w), 1547 (w), 1454 (m), 1382 (w), 1260 (m), 1092 (s), 1039 (vs), 910 (w), 804 (s), 724 (m).

Calculated for C$_{60}$H$_{120}$B$_{18}$Na$_6$O$_{10}$: C, 54.01; H, 9.07, and found: C, 54.21; H, 9.01.

EXAMPLE 3

Preparation of Me$_2$C(C$_5$H$_5$)(C$_2$B$_9$H$_{12}$)

85% H$_3$PO$_4$ (10.20 g, 88.5 mmol) was added to a suspension of [{[(μ-η$^5$): η$^5$-Me$_2$C(C$_5$H$_4$)(C$_2$B$_9$H$_{10}$)]Na(THF)}{Na(THF)$_3$}{Na(THF)$_2$}]$_2$ (1.33 g, 1.0 mmol) in toluene (30 mL). The resulting two-phase mixture was vigorously stirred at room temperature for 2 h. The toluene layer was decanted and the H$_3$PO$_4$ layer was extracted with toluene (2×15 mL). The toluene solutions were combined and dried over MgSO$_4$. After removal of toluene under vacuum, the pale yellow solid was recrystallized from toluene/n-hexane to give the title complex as a yellow solid (0.35 g, 72%).

$^1$H NMR (CD$_2$Cl$_2$): δ 6.57–5.91 (m, 3H), 2.82–2.92 (m, 2H)(C$_5$H$_5$), 125 (s, 3H), 1.10 (s, 3H)((CH$_3$)$_2$C).

$^{11}$B NMR (CD$_2$Cl$_2$): δ 3.67 (2), −9.58 (2), −13.91 (1), −19.43 (1), −28.56 (3).

IR (KBr, cm$^{-1}$): ν$_{BH}$ 2550 (s).

Calculated for C$_{10}$H$_{22}$B$_9$: C, 50.13; H, 9.26, and found: C, 50.25; H, 8.96

EXAMPLE 4

Preparation of [η$^5$:η$^5$-Me$_2$C(C$_5$H$_4$)(C$_2$B$_9$H$_{10}$)]ZrCH$_2$Ph

To a THF (30 mL) solution of [{[(μ-η$^5$):η$^5$-Me$_2$C(C$_5$H$_4$)(C$_2$B$_9$H$_{10}$)]Na(THF)}{Na(THF)$_3$}{Na(THF)$_2$}]$_2$ (1.62 g, 1.0 mmmol) was slowly added a suspension of ZrCl$_4$(THF)$_2$ (0.76 g, 2.0 mmol) in THF (10 mL) at −78° C. and the mixture was slowly warmed to room temperature and stirred overnight. A THF (10 mL) solution of KCH$_2$C$_6$H$_5$ (0.25 g, 2.0 mmol) was then added dropwise at −78° C. The reaction mixture was slowly warmed to room temperature and stirred for four hours. After removal of the precipitates and 40 mL of THF, the title complex was isolated as orange crystals via hexane vapor diffusion (0.63 g, 75%).

$^1$H NMR (benzene-d$_6$): δ 7.48 (m, 2H), 7.31 (m, 2H), 6.92 (m, 1H)(CH$_2$C$_6$H$_5$), 6.68 (m, 1H), 6.27 (m, 1H), 6.24 (m, 1H), 4.93 (m, 1H)(C$_5$H$_4$), 2.60 (s, 2H)(CH$_2$C$_6$H$_5$), 1.99 (s, 1H)(CH of C$_2$B$_9$H$_{10}$), 1.41 (s, 3H), 0.84 (s, 3H)((CH$_3$)$_2$C).

$^{13}$C NMR (benzene-d$_6$): δ 155.0, 129.7, 127.1, 126.5, 122.8 (CH$_2$C$_6$H$_5$), 122.5, 121.6, 120.2, 108.6, 107.2 (C$_5$H$_4$), 68.3 (CH$_2$C$_6$H$_5$), 66.3, 51.6 (C$_2$B$_9$H$_{10}$), 38.2, 29.3, 26.3 ((CH$_3$)$_2$C).

$^{11}$B NMR (benzene-d$_6$): δ3.6 (1), −0.2 (1), −2.7 (1), −5.7 (2), −7.7 (1), −11.3 (1), −12.5 (1), −18.3 (1).

IR (KBr, cm$^{-1}$): ν 2953 (m), 2913 (m), 2533 (s), 1592 (w), 1457 (m), 1259 (s), 1193 (w), 1085 (vs), 1028 (vs), 862 (w), 805 (s).

Calculated for C$_{17}$H$_{27}$B$_9$Zr: C, 48.62; H, 6.48, and found: C, 48.87; H, 6.58.

EXAMPLE 5

Preparation of [η$^5$:η$^5$-Me$_2$C(C$_5$H$_4$)(C$_2$B$_9$H$_{10}$)]ZrCH$_2$SiMe$_3$ A toluene (15 mL) solution of Me$_2$C(C$_5$H$_5$)(C$_2$B$_9$H$_{12}$) (240 mg, 11.0 mmol) was slowly added to a toluene (20 mL) solution of Zr(CH$_2$TMS)$_4$ (440 mg, 1.0 mmol) with stirring at −78° C. The reaction mixture was stirred overnight at room temperature. This solution was concentrated under vacuum to about 15 mL from which the title complex was isolated as pale-yellow crystals (253 mg, 61%).

$^1$H NMR (benzene-d$_6$): δ 6.65 (m, 1H), 6.23 (m, 1H), 6.20 (m, 1H), 5.91 (m, 1H)(C$_5$H$_4$), 2.10 (d, J=9.0 Hz, 1H)(CH$_2$SiMe$_3$), 1.97 (s, 1H)(CH of C$_2$B$_9$H$_{10}$), 1.82 (d, J=9.0 Hz, 1H)(CH$_2$SiMe$_3$), 1.40 (s, 3H), 0.82 (s, 3H)((CH$_3$)$_2$C).

$^{11}$B NMR (benzene-d$_6$): δ 3.3 (1), −0.1 (1), −2.5 (1), −5.7 (2), −7.6 (1), −11.1 (1), −12.2 (1), −18.1 (1).

IR (KBr, cm$^{-1}$): ν 2961 (m), 2921 (m), 2553 (s), 1230 (s), 1152 (w), 1088 (vs), 853 (w), 8795 (s).

Calculated for C$_{14}$H$_{31}$B$_9$SiZr: C, 40.42; H, 7.51, and found: C, 40.61; H, 7.46.

Alternative Method

The title complex was also prepared as pale-yellow crystals from [{[(μ-η$^5$):η$^5$-Me$_2$C(C$_5$H$_4$)(C$_2$B$_9$H$_{10}$)]Na(THF)}{Na(THF)$_3$}{Na(THF)$_2$}]$_2$ (1.62 g, 1.0 mmmol), ZrCl$_4$(THF)$_2$ (0.76 g, 2.0 mmol) and LiCH$_2$SiMe$_3$ (11.0M in pentane, 2.0 mmol) in 30 mL of THF using the procedure identical to that described for [η$^5$:η$^5$-Me$_2$C(C$_5$H$_4$)(C$_2$B$_9$H$_{10}$)]ZrCH$_2$Ph in Example 4: yield 0.65 g (78%).

EXAMPLE 6

Preparation of [η$^5$:η$^5$-Me$_2$C(C$_9$H$_6$)(C$_2$B$_9$H$_{10}$)]Zr(NHC$_6$H$_3$Me$_2$-2,6)(THF)

To a THF (25 mL) solution of [Me$_2$C(C$_9$H$_7$)(C$_2$B$_9$H$_{11}$)][Me$_3$NH] (0.336 g, 0.96 mmol) was added NaH (0.18 g, 7.5 mmol) and the reaction mixture was refluxed for 2 days. After removal of excess NaH by filtration, the resulting solution was added to a suspension of ZrCl$_4$(THF)$_2$ (0.362 g, 0.96 mmol) in THF (10 mL) at −78° C. and the mixture was slowly warmed to room temperature and stirred overnight.

After removal of the precipitate, to the resulting THF solution was added a THF (5 mL) solution of NaNHC$_6$H$_3$Me$_2$-2,6 (0.137 g, 0.96 mmol) at −78° C., and the reaction mixture was stirred at room temperature for 2 days. The solvent was evaporated under vacuum and the residue was extracted with toluene (15 mL ×3). The toluene solutions were combined and concentrated to about 10 mL. The title complex was isolated as yellow crystals after this solution stood at room temperature for several days (0.32 g, 58%).

$^1$H NMR (pyridine-d$_5$): δ 9.38 (s, 1H)(NH), 7.86 (d, J=9 Hz, 1H), 7.37 (d, J=8.4 Hz, 1H), 6.96 (m, 1H), 6.91 (m, 1H), 6.86–6.75 (m, 2H)(C$_9$H$_6$), 7.04 (d, J=7.5 Hz, 2H), 6.41 (m, 1H)(NHC$_6$H$_3$(CH$_3$)$_2$)). 3.64 (m, 4H), 1.59 (m, 4H)(THF), 3.35 (s, 1H)(CH of C$_2$B$_9$H$_{10}$), 2.31 (s, 6H)(NHC$_6$H$_3$(CH$_3$)$_2$), 1.99 (s, 3H), 1.70 (s, 3H)((CH$_3$)$_2$C).

$^{13}$C NMR (pyridine-d$_5$): δ 154.0, 129.8, 127.7, 126.5, 125.3, 124.7, 123.8, 121.9, 120.8, 118.9, 114.7, 111.8, 110.3, 108.9 (NHC$_6$H$_3$(CH$_3$)$_2$+C$_9$H$_6$), 67.1, 25.1 (THF), 51.1 (C$_2$B$_9$H$_{10}$), 40.7, 29.0, 28.9 ((CH$_3$)$_2$C), 20.1, 17.3 (NHC$_6$H$_3$(CH$_3$)$_2$).

$^{11}$B NMR (pyridine-d$_5$): δ4.5 (1), −3.3 (1), −4.6 (1), −6.7 (2), −11.5 (3), −18.6 (1).

IR (KBr, cm$^{-1}$): $v_{BH}$2524 (s).

Calculated for C$_{26}$H$_{46}$B$_9$NOZr: C, 54.10; H, 8.03; N, 2.43, and found: C, 54.33; H, 7.87; N, 2.32.

EXAMPLE 7

Preparation of [η$^5$:η$^5$-Me$_2$C(C$_9$H$_6$)(C$_2$B$_9$H$_{10}$)]Zr(CH$_2$C$_6$H$_5$)

To a THF (15 mL) solution of [Me$_2$C(C$_9$H$_7$)(C$_2$B$_9$H$_{11}$)][Me$_3$NH] (0.30 g, 0.86 mmol) was added NaH (0.16 g, 6.66 mmol) and the reaction mixture was refluxed for 2 days. The excess NaH was filtered off and washed with THF (3 mL ×2). The filtrate was added to a suspension of ZrCl$_4$(THF)$_2$ (0.325 g, 0.86 mmol) in THF (10 mL) at −78° C. and the mixture was slowly warmed to room temperature and stirred overnight. After removal of the precipitate, the filtrate was added to a THF (10 mL) solution of KCH$_2$C$_6$H$_5$ (0.11 g, 0.86 mmol) at −78° C., and the reaction mixture was slowly warmed to room temperature and stirred overnight. The solvent was evaporated under vacuum and the residue was extracted with DME (5 mL ×3). The DME solutions were combined and concentrated to about 5 mL, form which the title complex was isolated as orange crystals (0.26 g, 65%).

$^1$H NMR (benzene-d$_6$): δ 7.74 (d, J=9 Hz, 1H), 7.49 (m, 2H), 7.39 (m, 2H), 7.23–6.80 (m, 4H), 6.71 (d, J=3.6 Hz, 1H), 5.27 (m, J=3.6 Hz, 1H)(CH$_2$C$_6$H$_5$+C$_9$H$_6$), 2.60 (s, 2H)(CH$_2$C$_6$H$_5$), 2.20 (s, 1H)(CH of C$_2$B$_9$H$_{10}$), 1.81 (s, 3H), 1.12 (s, 3H)((CH$_3$)$_2$C).

$^{13}$CNMR (benzene-d$_6$): δ 154.8, 130.3, 129.3, 127.0, 126.5, 126.0, 125.6, 124.6, 123.9, 122.1, 121.3, 115.8, 112.4, 104.6 (CH$_2$C$_6$H$_5$+C$_9$H$_6$), 70.3 (CH$_2$C$_6$H$_5$), 65.3, 52.0 (C$_2$B$_9$H$_{10}$), 40.7, 29.7, 29.4 ((CH$_3$)$_2$C).

$^{11}$B NMR (benzene-d$_6$): δ0.9 (1), −0.8 (1), −2.7 (1), −5.5 (1), −7.0 (2), −11.3 (1), −13.3 (1), −20.1 (1).

IR (KBr, cm$^{-1}$): $v_{BH}$ 2533 (vs).

Calculated for C$_{21}$H$_{29}$B$_9$Zr: C, 53.67; H, 6.22, and found: C, 53.55; H, 6.16.

EXAMPLE 8

Preparation of [CH$_2$(C$_5$H$_3$Bu$_2^t$-2,5)(C$_2$B$_9$H$_{11}$)][Me$_3$NH]

Figure 3:
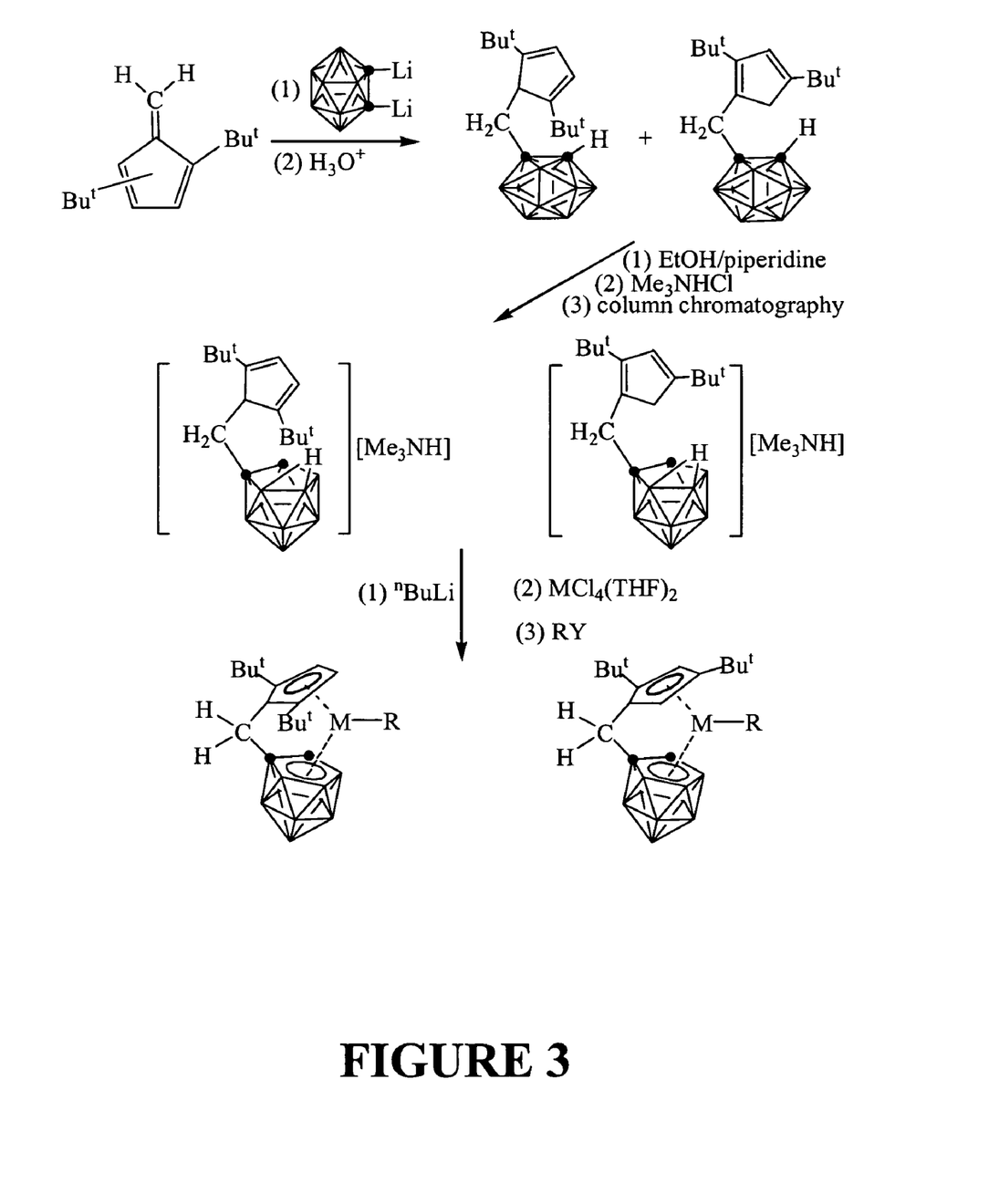
FIG. 3 illustrates another preferred reaction scheme for producing complexes of formula (I) using a disubstituted fulvene as a starting material.

As shown in FIG. 3, this complex was prepared from CH$_2$(C$_5$H$_3$Bu$_2^t$-2,5)(C$_2$B$_{10}$H$_{11}$)(0.385 g, 1.15 mmol) and piperidine (3.0 mL, 30.0 mmol) in ethanol (20 mL) using the same procedure as described for the synthesis of [Me$_2$C(C$_5$H$_5$)(C$_2$B$_9$H$_{11}$)][Me$_3$NH] in Example 1. The product was further purified by recrystallization from ethanol/hexane to yield the title complex as a white solid (0.41 g, 93%).

$^1$H NMR (acetone-d$_5$): δ 6.39 (m, 1H), 6.14 (m, 1H) (C$_5$H$_3$), 3.22 (s, 11H) ((CH$_3$)$_3$NH+CH$_2$), 3.01 (s, 1H) (C$_5$H$_3$), 1.70 (s, 1H)(CH of C$_2$B$_9$H$_{11}$), 1.25 (s, 6H), 1.20 (s, 3H), 1.00 (s, 3H), 0.94 (s, 6H)((CH$_3$)$_3$C), −2.8 (br s, 1H)(B—H—B).

$^{13}$C NMR (acetone-d$_5$): δ 148.4, 143.4, 142.7, 135.7, 134.3 (C$_5$H$_3$), 65.4 (C$_2$B$_9$H$_{10}$), 64.9 (C$_5$H$_3$), 46.5 ((CH$_3$)$_3$NH), 38.4, 38.3 (CH$_2$), 34.6, 34.4, 32.1, 31.9 ((CH$_3$)$_3$C).

$^{11}$B NMR (acetone-d$_5$): δ −15.1 (1), −16.4 (1), −18.8 (1), −21.1 (1), −23.7 (2), −28.3 (1), −38.7 (1), −41.7 (1).

IR (KBr, cm$^{-1}$): $v_{BH}$ 2529 (vs).

Calculated for C$_{19}$H$_{44}$B$_9$N: C, 59.45; H, 11.55; N, 3.65, and found: C, 59.32; H, 11.51; N, 3.71.

EXAMPLE 9

Preparation of [CH$_2$(C$_5$H$_3$Bu$^t_2$-2,4)(C$_2$B$_9$H$_{11}$)][Me$_3$NH]

This complex was prepared from CH$_2$(C$_5$H$_3$Bu$_2^t$-2,4)(C$_2$B$_{10}$H$_{11}$)(0.77 g, 2.30 mmol) and piperidine (6.0 mL, 60.0 mmol) in ethanol (20 mL) using the same procedure described in Example 8. The product was purified by recrystallization from ether/hexane (2:1) to yield the title complex as a white solid (0.79 g, 89%).

$^1$H NMR (acetone-d$_5$): δ 6.35 (s), 6.06 (s)(C$_5$H$_3$), 3.21 (s, 11H)((CH$_3$)$_3$NH+CH$_2$), 2.93 (m, 2H)(C$_5$H$_3$), 1.70 (s, 1H) (CH of C$_2$B$_9$H$_{11}$), 1.15 (m, 18H)((CH$_3$)$_3$C), −2.7 (br s, 1H)(B-H-B).

$^{13}$C NMR (acetone-d$_5$): δ 155.2, 153.6, 145.1, 144.2, 140.2, 130.0, 129.1, 126.2 (C$_5$H$_3$), 57.9 (C$_2$B$_9$H$_{10}$), 46.5 ((CH$_3$)$_3$NH), 45.4, 41.8 (C$_5$H$_3$), 40.7, 40.2 (CH$_2$), 33.8, 33.7, 32.0, 31.9, 31.6, 31.5 ((CH$_3$)$_3$C).

$^{11}$B NMR (acetone-d$_5$): δ −9.3 (1), −10.9 (1), −13.3 (1), −16.1 (1), −19.1 (2), −22.0 (1), −33.3 (1), −36.4 (1).

IR (KBr, cm$^{-1}$): $v_{BH}$ 2520 (vs).

Calculated for C$_{19}$H$_{44}$B$_9$N: C, 59.45; H, 11.55; N, 3.65, and found: C, 59.56; H, 11.33; N, 3.46.

EXAMPLE 10

Preparation of [η$^5$:η$^5$-CH$_2$(C$_5$H$_2$Bu$_2^t$-2,4)(C$_2$B$_9$H$_{10}$)]Zr(CH$_2$C$_6$H$_5$)

To a THF (20 mL) solution of [CH$_2$(C$_5$H$_3$Bu$_2^t$-2,4)(C$_2$B$_9$H$_{11}$)][Me$_3$NH](0.79 g, 2.06 mmol) was added KH (0.67 g, 16.7 mmol) and the reaction mixture was refluxed for 2 days. The excess KH was filtered off and washed with THF (3 mL ×2). The filtrate was added to a suspension of ZrCl$_4$(THF)$_2$ (0.78 g, 2.06 mmol) in THF (20 mL) at −78° C. and the mixture was slowly warmed to room temperature and stirred overnight. After removal of the precipitate, the filtrate was added to a THF (10 mL) solution of KCH$_2$C$_6$H$_5$ (0.27 g, 2.07 mmol) at −78° C., and the reaction mixture was slowly warmed to room temperature and stirred overnight. The solvent was evaporated under vacuum and the residue was extracted with toluene (10 mL ×3). The toluene solutions were combined and concentrated to about 8 mL, from which the title complex was isolated as yellow crystals (0.71 g, 68%).

$^1$H NMR (benzene-$d_6$): δ 7.51 (m, 2H), 7.37 (m, 2H), 6.98 (m, 1H)($CH_2C_6H_5$), 6.58 (s, 1H), 6.34 (s, 1H)($C_5H_4$), 2.84 (s, 2H)($CH_2$), 2.58 (s, 2H) ($CH_2C_6H_5$), 1.47 (s, 9H) ($C(CH_3)_3$), 1.24 (s, 9H)($C(CH_3)_3$).

$^{13}$C NMR (benzene-$d_6$): δ 155.0, 129.7, 127.1, 126.5, 122.8 ($CH_2C_6H_5$), 143.1, 137.1, 125.9, 122.5 ($C_5H_3$), 68.3 ($CH_2C_6H_5$), 56.6 ($C_2B_{10}H_{11}$), 37.2 ($CH_2$), 36.8, 33.8, 33.4 (($CH_3)_3C$).

$^{11}$B NMR (benzene-$d_6$): δ 4.36 (1), −3.15 (1), −4.45 (1), −8.25 (2), −9.65 (2), IR (KBr, cm$^{-1}$): $v_{BH}$ 2533 (s).

Calculated for $C_{23}H_{37}B_9Zr$: C, 55.02; H, 7.43; and found: C, 55.35; H, 7.22.

EXAMPLE 11

Preparation of [$H_2C(C_5HMe_4)(C_2B_9H_{11})$][$Me_3NH$]

Figure 4:
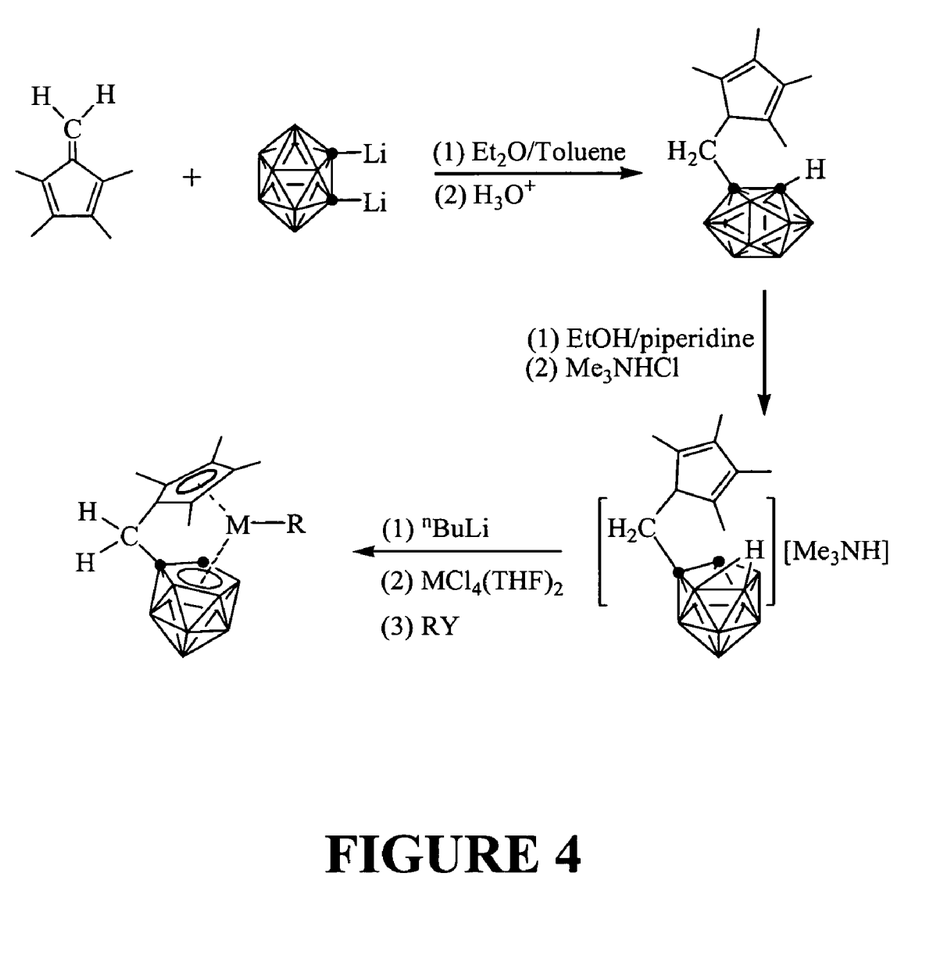
FIG. 4 illustrates another preferred reaction scheme for producing complexes of formula (I) using a tetrasubstituted fulvene as a starting material.

As shown in FIG. 4, to an ethanol (40 mL) solution of $H_2C(C_5HMe_4)(C_2B_{10}H_{11})$(0.85 g, 3.0 mmol) was added piperidine (7.5 mL, 75.0 mmol). The mixture was refluxed for 2 days until the $^{11}$B NMR spectrum of the solution showing no peaks corresponding to the starting material. The ethanol and excess piperidine were removed under vacuum, the residue was dissolved in ethanol (5 mL). After filtration, a saturated trimethylammonium hydride chloride solution was added. The sticky solid was filtered off, washed with water and hexane respectively, reprecipitated from acetone to ether, and dried in vacuum for 3 hrs to give the title complex as pale yellow oil (0.78 g, 78%).

$^1$H NMR (CDCl$_3$): δ 3.13 (s, 9H)($CH_3$ of [$Me_3NH$]), 3.10 (s, 2H)($CH_2$), 1.83 (d, 3H)($CH_3$), 1.72 (m, 6H)($CH_3$), 1.00 (m, 3H)($CH_3$).

$^{13}$C NMR (CDCl$_3$): δ 142.3, 136.4, 131.9, 131.6 ($C_5Me_4$), 63.7, 48.2 ($C_2B_{10}H_{11}$), 47.8 ($CH_2$), 43.4 ([($CH_3)_3NH$]), 33.7 ($C_5Me_4$), 13.1, 12.5, 9.4, 8.8 ($C_5(CH_3)_4$).

$^{11}$B NMR (acetone-$d_5$): δ −9.9 (1), −10.9 (1), −14.0 (1), −16.9 (1), −18.3 (1), −19.1 (1), −22.3 (1), −33.4 (1), −36.6 (1).

IR (KBr, cm$^{-1}$): $v_{BH}$ 2508 (vs).

Calculated for $C_{15}H_{36}B_9N$: C, 54.97; H, 11.07; N, 4.27, and found: C, 54.68; H, 11.23; N, 4.31.

EXAMPLE 12

Preparation of [$\eta^5$:$\eta^5$-$H_2C(C_5Me_4)(C_2B_9H_{10})$]Zr($CH_2TMS$)

To a THF (40 mL) solution of [$H_2C(C_5HMe_4)(C_2B_9H_{11})$][$Me_3NH$] (426 mg, 1.3 mmol) was slowly added $^n$BuLi (4.0 mL, 3.9 mmol) at −78° C. and the mixture was slowly warmed to room temperature. The resultant clear yellow solution was slowly added to a suspension of $ZrCl_4(THF)_2$ (490 mg, 1.3 mmol) in THF (10 mL) at −78° C. The mixture was slowly warmed to room temperature and stirred overnight. To the resultant solution was slowly added a 1.0 M solution of $LiCH_2SiMe_3$ in pentane (1.3 mL, 1.3 mmol) at −78° C. The mixture was slowly warmed to room temperature and stirred overnight. After removal of solvent, the residue was extracted with toluene (15 mL ×3). The toluene solutions were combined and concentrated to about 10 mL from which the title complex was isolated as yellow crystals (415 mg, 72%).

$^1$H NMR (benzene-$d_6$): δ 2.95 (d, J=14.7 Hz, 1H), 2.63 (d, J=14.7 Hz, 1H) ($CH_2$), 2.14 (s, 3H)($CH_3$), 2.07 (s, 3H)($CH_3$), 2.02 (s, 3H)($CH_3$), 1.69 (s, 3H)($CH_3$), 0.81 (d, J=9.0 Hz, 1H), 0.63 (d, J=9.0 Hz, 1H)($CH_2TMS$), 0.38 (s, 9H)($CH_2Si(CH_3)_3$).

$^{13}$C NMR (benzene-$d_6$): δ 124.2, 122.9, 116.8, 113.4, 103.9 ($C_5Me_4$), 64.5 ($CH_2Si(CH_3)_3$), 61.9, 49.0 ($C_2B_{10}H_{11}$), 33.3 ($CH_2$), 14.1, 12.8, 12.5, 12.4 ($C_5(CH_3)_4$), 4.2 ($CH_2Si(CH_3)_3$).

$^{11}$B NMR (benzene-$d_6$): δ 0.08 (1), −6.21 (2), −10.12 (1), −13.69 (2), −15.91 (1), −18.90 (1), −22.95 (1).

Calculated for $C_{16}H_{35}B_9SiZr$: C, 43.28; H, 7.95, and found: C, 43.36; H, 7.85.

EXAMPLE 13

Preparation of [$\eta^5$:$\eta^5$-$H_2C(C_5Me_4)(C_2B_9H_{10})$]Hf($CH_2TMS$)

This complex was prepared as pale yellow crystals from [$H_2C(C_5HMe_4)(C_2B_9H_{11})$][$Me_3NH$] (426 mg, 1.3 mmol), $^n$BuLi (4.0 mL, 3.9 mmol), $HfCl_4(THF)_2$ (605 mg, 1.3 mmol) and $LiCH_2SiMe_3$ (1.3 mL, 1.3 mmol) in THF using the same procedure described in Example 12: yield 428 mg (62%).

$^1$H NMR (benzene-$d_6$): δ 2.92 (d, J=14.7 Hz, 1H), 2.60 (d, J=14.7 Hz, 1H) ($CH_2$), 2.15 (s, 3H)($CH_3$), 2.05 (s, 3H)($CH_3$), 2.00 (s, 3H)($CH_3$), 1.72 (s, 3H)($CH_3$), 0.95 (d, J=9.0 Hz, 1H), 0.68 (d, J=9.0 Hz, 1H)($CH_2TMS$), 0.46 (s, 9H)($CH_2Si(CH_3)_3$).

$^{13}$C NMR (benzene-$d_6$): δ 124.1, 122.5, 116.6, 113.5, 103.7 ($C_5Me_4$), 64.8 ($CH_2Si(CH_3)_3$), 61.9, 51.0 ($C_2B_{10}H_{11}$), 33.8 ($CH_2$), 14.0, 12.5, 12.6, 12.2 ($C_5(CH_3)_4$), 4.0 ($CH_2Si(CH_3)_3$).

$^{11}$B NMR (benzene-$d_6$): δ 0.18 (1), −6.16 (2), −10.10 (1), −13.50 (2), −15.86 (1), −18.75 (1), −21.98 (1).

Calculated for $C_{16}H_{35}B_9HfSi$: C, 36.17; H, 6.64, and found: C, 36.33; H, 6.75.

EXAMPLE 14

Ethylene Polymerization (in the Absence of MAO)

This experiment was carried out in a 150 mL glass reactor equipped with a magnetic stirrer and gas inlets. The reactor was charged with the catalyst [$\eta^5$:$\eta^5$-$Me_2C(C_5H_4)(C_2B_9H_{10})$]$ZrCH_2Ph$ (3.0 μmol) and toluene (50 mL). Ethylene gas was then introduced to the reactor at 25° C., and its pressure was maintained continuously at 1 atm by means of bubbling. The polymerization was terminated after 1 h by addition of acidic ethanol (100 mL). The white precipitate was filtered off and washed with ethanol and acetone. The resulting powder was finally dried in a vacuum oven at 80° C. overnight. $M_w$ and $M_n$ were 4.86×10$^4$ and 2.21×10$^4$, respectively, and $M_w/M_n$=2.20. Catalyst activity was 4.64×10$^6$ g polymer/mol Zr-hr-atm ethylene.

EXAMPLE 15

Ethylene Polymerization (in the Presence of MAO)

Ethylene was polymerized as in Example 14 except that methylalumoxane (MAO) was employed as a potential cocatalyst. The reaction mixture contained an Al/Zr ratio of 1,000. Catalyst activity was 4.85×10⁶ g polymer/mol Zr-hr-atm ethylene, showing that activity remains almost the same in the presence of MAO. This suggests that MAO is not an effective cocatalyst.

Other ligands and catalysts shown in Schemes 1–4 were prepared in a similar manner described above.

The specific embodiments described herein are offered by way of examples only. Many modifications and variations of the embodiments described herein may be made without departing from the scope, as is apparent to those skilled in the art.

What is claimed is:

1. A bridged cyclopentadienyl-dicarbollide metallocene complex having the formula (I):

$$\{L[(Cp)(C_2B_9R^1{}_{10})]\}MR \qquad (I)$$

wherein:
Cp is a group selected from the group consisting of cyclopentadienyl, indenyl, tetrahydroindenyl, and fluorenyl,
  wherein said Cp group is unsubstituted or substituted by one or more radicals selected from the group consisting of $C_1$–$C_{10}$ alkyl, $C_2$–$C_{10}$ alkenyl, $C_3$–$C_{10}$ cycloalkyl, $C_1$–$C_{10}$ alkoxy, and $C_6$–$C_{15}$ aryl, where each pair of adjacent radicals on the ring together may form a cyclic group;
each $R^1$ is independently hydrogen, halogen, $C_1$–$C_{10}$ alkyl, or $C_2$–$C_{10}$ alkenyl;
L is $C_1$–$C_4$ alkylene, which is unsubstituted or substituted by one or more radicals selected form the group consisting of $C_1$–$C_{10}$ alkyl, $C_2$–$C_{10}$ alkenyl, $C_3$–$C_{10}$ cycloalkyl, $C_1$–$C_{10}$ alkoxy, $C_6$–$C_{15}$ aryl, and $Si(R^2)_2$, wherein each $R^2$ is independently selected from the group consisting of hydrogen, $C_1$–$C_{10}$ alkyl, $C_2$–$C_{10}$ alkenyl, $C_1$–$C_{10}$ alkoxy, $C_3$–$C_{10}$ cycloalkyl, and $C_6$–$C_{15}$ aryl, wherein L bonds to both Cp ring and the cage of $C_2B_9R^1{}_{10}$;
R is selected from the group consisting of hydrogen, halogen, $R^3$, $OR^3$, $SR^3$, $NR^3R^4$, $PR^3R^4$, and $ZSiR^3(R^4)_2$,
  wherein each $R^3$ is independently selected from the group consisting of $C_1$–$C_{10}$ alkyl, $C_2$–$C_{10}$ alkenyl, $C_3$–$C_{10}$ cycloalkyl, and $C_6$–$C_{15}$ aryl, and
  each $R^4$ is independently selected from the group consisting of hydrogen, $C_1$–$C_{10}$ alkyl, $C_2$–$C_{10}$ alkenyl, $C_3$–$C_{10}$ cycloalkyl and $C_6$–$C_{15}$ aryl, and Z is $C_1$–$C_{10}$ alkylene; and
M is Ti, Zr, or Hf.

2. The complex of claim 1, wherein Cp is cyclopentadienyl or indenyl, wherein said cyclopentadienyl and indenyl is unsubstituted or substituted with one to four substituents selected from the group consisting of $C_1$ to $C_4$ alkyl, $C_2$ to $C_4$ alkenyl, $C_3$ to $C_6$ cycloalkyl, $C_1$ to $C_4$ alkoxy, and $C_6$–$C_{10}$ aryl, and
  wherein $R^1$ is hydrogen.

3. The complex of claim 2, wherein Cp is $C_5H_4$, $C_5Me_4$, $C_5H_2(Pr^i)_2$, $C_5H_2(Bu^t)_2$ or $C_9H_6$.

4. The complex of claim 1, wherein L is $C_1$–$C_4$ alkylene, wherein said $C_1$–$C_4$ alkylene is unsubstituted or substituted with one or more radicals selected from the group consisting of $C_1$–$C_4$ alkyl, $C_2$–$C_4$ alkenyl, $C_3$–$C_6$ cycloalkyl, $C_1$–$C_4$ alkoxy, $C_6$–$C_{10}$ aryl, and $Si(R^2)_2$, wherein each $R^2$ is independently selected from the group consisting of hydrogen, $C_1$–$C_4$ alkyl, $C_2$–$C_4$ alkenyl, $C_3$–$C_6$ cycloalkyl, $C_1$–$C_4$ alkoxy, and $C_6$–$C_{10}$ aryl;
wherein Cp is $C_5H_4$, $C_5Me_4$, $C_5H_2(Pr^i)_2$, $C_5H_2(Bu^t)_2$ or $C_9H_6$; and
wherein $R^1$ is hydrogen.

5. The complex of claim 4, wherein L is $CMe_2$ or $CH_2$.

6. The complex of claim 1, wherein R is selected from the group consisting of $R^3$, $OR^3$, $SR^3$, $NR^3R^4$, $PR^3R^4$, and $ZSiR^3(R^4)_2$,
  wherein each $R^3$ is independently selected from the group consisting of $C_1$–$C_4$ alkyl, $C_2$–$C_4$ alkenyl, $C_3$–$C_6$ cycloalkyl and $C_6$–$C_8$ aryl, and
  wherein each $R^4$ is independently selected from the group consisting of hydrogen, $C_1$–$C_4$ alkyl, $C_2$–$C_4$ alkenyl, $C_3$–$C_6$ cycloalkyl and $C_6$–$C_8$ aryl, and
  Z is $C_1$–$C_4$ alkylene;
Cp is $C_5H_4$, $C_5Me_4$, $C_5H_2(Pr^i)_2$, $C_5H_2(Bu^t)_2$ or $C_9H_6$, and
$R^1$ is hydrogen.

7. The complex of claim 6, wherein R is selected from the group consisting of $R^3$, $OR^3$, $NR^3R^4$ and $ZSiR^3(R^4)_2$ wherein each $R^3$ is independently selected from the group consisting of $C_1$–$C_4$ alkyl and $C_6$–$C_8$ aryl, and wherein each $R^4$ is independently selected from the group consisting of hydrogen, $C_1$–$C_4$ alkyl and $C_6$–$C_8$ aryl, and Z is $C_1$–$C_4$ alkylene.

8. The complex of claim 7, wherein R is $CH_2Ph$, $CH_2Si(CH_3)_3$, or $NHC_6H_3Me_2$-2,6.

9. The complex of claim 1, wherein M is Zr or Hf; Cp is $C_5H_4$, $C_5Me_4$, $C_5H_2(Pr^i)_2$, $C_5H_2(Bu^t)_2$ or $C_9H_6$; and $R^1$ is hydrogen.

10. The complex of claim 1, wherein L is $CMe_2$ or $CH_2$; Cp is $C_5H_4$ or $C_9H_6$; R is $CH_2Ph$, $CH_2Si(CH_3)_3$, or $NHC_6H_3Me_2$-2,6; $R^1$ is H; and M is Zr or Hf.

11. The complex of claim 1, which is selected from the group consisting of:
[η⁵:η⁵-Me₂C(C₅H₄)(C₂B₉H₁₀)]Zr(CH₂C₆H₅),
[η⁵:η⁵-Me₂C(C₅H₄)(C₂B₉H₁₀)]Zr(CH₂SiMe₃),
[η⁵:η⁵-Me₂C(C₉H₆)(C₂B₉H₁₀)]Zr(NHC₆H₃Me₂-2,6),
[η⁵:η⁵-Me₂C(C₉H₆)(C₂B₉H₁₀)]Zr(CH₂C₆H₅),
[η⁵:η⁵-CH₂(C₅H₂Bu^t₂-2,4)(C₂B₉H₁₀)]Zr(CH₂C₆H₅),
[η⁵:η⁵-H₂C(C₅Me₄)(C₂B₉H₁₀)]Zr(CH₂SiMe₃), and
[η⁵:η⁵-H₂C(C₅Me₄)(C₂B₉H₁₀)]Hf(CH₂SiMe₃).

12. A method for preparing a bridged cyclopentadienyl-dicarbollide metallocene complex of formula (I):

$$\{L[(Cp)(C_2B_9R^1{}_{10})]\}MR \qquad (I)$$

wherein:
Cp is a group selected from the group consisting of cyclopentadienyl, indenyl, tetrahydroindenyl, and fluorenyl,
  wherein said Cp group is unsubstituted or substituted by one or more radicals selected from the group consisting of $C_1$–$C_{10}$ alkyl, $C_2$–$C_{10}$ alkenyl, $C_3$–$C_{10}$ cycloalkyl, $C_1$–$C_{10}$ alkoxy, and $C_6$–$C_{15}$ aryl, where each pair of adjacent radicals on the ring together may form a cyclic group;
each $R^1$ is independently hydrogen, halogen, $C_1$–$C_{10}$ alkyl, or $C_2$–$C_{10}$ alkenyl;
L is $C_1$–$C_4$ alkylene, which is unsubstituted or substituted by one or more radicals selected form the group consisting of $C_1$–$C_{10}$ alkyl, $C_2$–$C_{10}$ alkenyl, $C_3$–$C_{10}$ cycloalkyl, $C_1$–$C_{10}$ alkoxy, $C_6$–$C_{15}$ aryl, and $Si(R^2)_2$, wherein each $R^2$ is independently selected from the group consisting of hydrogen, $C_1$–$C_{10}$ alkyl, $C_2$–$C_{10}$ alkenyl, $C_1$–$C_{10}$ alkoxy, $C_3$–$C_{10}$ cycloalkyl, and $C_6$–$C_{15}$ aryl, wherein L bonds to both Cp ring and the cage of $C_2B_9R^1{}_{10}$;

R is selected from the group consisting of hydrogen, halogen, $R^3$, $OR^3$, $SR^3$, $NR^3R^4$, $PR^3R^4$, and $ZSiR^3(R^4)_2$,
  wherein each $R^3$ is independently selected from the group consisting of $C_1$–$C_{10}$ alkyl, $C_2$–$C_{10}$ alkenyl, $C_3$–$C_{10}$ cycloalkyl, and $C_6$–$C_{15}$ aryl, and
  each $R^4$ is independently selected from the group consisting of hydrogen, $C_1$–$C_{10}$ alkyl, $C_2$–$C_{10}$ alkenyl, $C_3$–$C_{10}$ cycloalkyl and $C_6$–$C_{15}$ aryl, and Z is $C_1$–$C_{10}$ alkylene; and
M is Ti, Zr, or Hf,
  the method comprising reacting a protonated form of $\{L[(Cp)(C_2B_9R^1{}_{10})]\}^{3-}$ with $MR_4$, wherein L, Cp, R, $R^1$ or M has the same definition as the above with the proviso that R is different from halogen, or
  reacting $\{L[(Cp)(C_2B_9R^1{}_{10})]\}^{3-}$ with $MX_4$, followed by substituting X with R if necessary, wherein R is different from halogen and X represents halogen.

13. The method of claim 12, wherein Cp is cyclopentadienyl or indenyl, wherein said cyclopentadienyl and indenyl is unsubstituted or substituted with one to four substituents selected from the group consisting of $C_1$ to $C_4$ alkyl, $C_2$ to $C_4$ alkenyl, $C_3$ to $C_6$ cycloalkyl, $C_1$ to $C_4$ alkoxy, and $C_6$–$C_{10}$ aryl, and
  wherein $R^1$ is hydrogen.

14. The method of claim 13, wherein Cp is $C_5H_4$, $C_5Me_4$, $C_5H_2(Pr^i)_2$, $C_5H_2(Bu^t)_2$ or $C_9H_6$.

15. The method of claim 12, wherein L is $C_1$–$C_4$ alkylene, wherein said $C_1$–$C_4$ alkylene is unsubstituted or substituted with one or more radicals selected from the group consisting of $C_1$–$C_4$ alkyl, $C_2$–$C_4$ alkenyl, $C_3$–$C_6$ cycloalkyl, $C_1$–$C_4$ alkoxy, $C_6$–$C_{10}$ aryl, and $Si(R^2)_2$, wherein each $R^2$ is independently selected from the group consisting of hydrogen, $C_1$–$C_4$ alkyl, $C_2$–$C_4$ alkenyl, $C_3$–$C_6$ cycloalkyl, $C_1$–$C_4$ alkoxy, and $C_6$–$C_{10}$ aryl;
  wherein Cp is $C_5H_4$, $C_5Me_4$, $C_5H_2(Pr^i)_2$, $C_5H_2(Bu^t)_2$ or $C_9H_6$; and
  wherein $R^1$ is hydrogen.

16. The method of claim 15, wherein L is $CMe_2$ or $CH_2$.

17. The method of claim 12, wherein R is selected from the group consisting of $R^3$, $OR^3$, $SR^3$, $NR^3R^4$, $PR^3R^4$, and $ZSiR^3(R^4)_2$,
  wherein each $R^3$ is independently selected from the group consisting of $C_1$–$C_4$ alkyl, $C_2$–$C_4$ alkenyl, $C_3$–$C_6$ cycloalkyl and $C_6$–$C_8$ aryl, and
  wherein each $R^4$ is independently selected from the group consisting of hydrogen, $C_1$–$C_4$ alkyl, $C_2$–$C_4$ alkenyl, $C_3$–$C_6$ cycloalkyl and $C_6$–$C_8$ aryl, and
  Z is $C_1$–$C_4$ alkylene; Cp is $C_5H_4$, $C_5Me_4$, $C_5H_2(Pr^i)_2$, $C_5H_2(Bu^t)_2$ or $C_9H_6$, and
  $R^1$ is hydrogen.

18. The method of claim 17, wherein R is selected from the group consisting of $R^3$, $OR^3$, $NR^3R^4$ and $ZSiR^3(R^4)_2$ wherein each $R^3$ is independently selected from the group consisting of $C_1$–$C_4$ alkyl and $C_6$–$C_8$ aryl, and wherein each $R^4$ is independently selected from the group consisting of hydrogen, $C_1$–$C_4$ alkyl and $C_6$–$C_8$ aryl, and Z is $C_1$–$C_4$ alkylene.

19. The method of claim 18, wherein R is $CH_2Ph$, $CH_2Si(CH_3)_3$, or $NHC_6H_3Me_2$-2,6.

20. The method of claim 12, wherein M is Zr or Hf; Cp is $C_5H_4$, $C_5Me_4$, $C_5H_2(Pr^i)_2$, $C_5H_2(Bu^t)_2$, or $C_9H_6$; and $R^1$ is hydrogen.

21. The method of claim 12, wherein L is $CMe_2$ or $CH_2$; Cp is $C_5H_4$ or $C_9H_6$; R is $CH_2Ph$, $CH_2Si(CH_3)_3$, or $NHC_6H_3Me_2$-2,6; $R^1$ is H; and M is Zr or Hf.

22. A process for olefin polymerization comprising contacting one or more olefin monomers with a complex having the formula (I):

$$\{L[(Cp)(C_2B_9R^1{}_{10})]\}MR \qquad (I)$$

wherein:
Cp is a group selected from the group consisting of cyclopentadienyl, indenyl, tetrahydroindenyl, and fluorenyl,
  wherein said Cp group is unsubstituted or substituted by one or more radicals selected from the group consisting of $C_1$–$C_{10}$ alkyl, $C_2$–$C_{10}$ alkenyl, $C_3$–$C_{10}$ cycloalkyl, $C_1$–$C_{10}$ alkoxy, and $C_6$–$C_{15}$ aryl, where each pair of adjacent radicals on the ring together may form a cyclic group;
each $R^1$ is independently hydrogen, halogen, $C_1$–$C_{10}$ alkyl, or $C_2$–$C_{10}$ alkenyl;
L is $C_1$–$C_4$ alkylene, which is unsubstituted or substituted by one or more radicals selected form the group consisting of $C_1$–$C_{10}$ alkyl, $C_2$–$C_{10}$ alkenyl, $C_3$–$C_{10}$ cycloalkyl, $C_1$–$C_{10}$ alkoxy, $C_6$–$C_{15}$ aryl, and $Si(R^2)_2$, wherein each $R^2$ is independently selected from the group consisting of hydrogen, $C_1$–$C_{10}$ alkyl, $C_2$–$C_{10}$ alkenyl, $C_1$–$C_{10}$ alkoxy, $C_3$–$C_{10}$ cycloalkyl, and $C_6$–$C_{15}$ aryl, wherein L bonds to both Cp ring and the cage of $C_2B_9R^1{}_{10}$;
R is selected from the group consisting of hydrogen, halogen, $R^3$, $OR^3$, $SR^3$, $NR^3R^4$, $PR^3R^4$, and $ZSiR^3(R^4)_2$,
  wherein each $R^3$ is independently selected from the group consisting of $C_1$–$C_{10}$ alkyl, $C_2$–$C_{10}$ alkenyl, $C_3$–$C_{10}$ cycloalkyl, and $C_6$–$C_{15}$ aryl, and
  each $R^4$ is independently selected from the group consisting of hydrogen, $C_1$–$C_{10}$ alkyl, $C_2$–$C_{10}$ alkenyl, $C_3$–$C_{10}$ cycloalkyl and $C_6$–$C_{15}$ aryl, and Z is $C_1$–$C_{10}$ alkylene; and
M is Ti, Zr, or Hf.

23. The process of claim 22, wherein L is $CMe_2$ or $CH_2$; Cp is $C_5H_4$ or $C_9H_6$; R is $CH_2Ph$, $CH_2Si(CH_3)_3$, or $NHC_6H_3Me_2$-2,6; $R^1$ is H; and M is Zr or Hf.

24. The process of claim 23, wherein the monomer is ethylene or an alpha olefin.

* * * * *